United States Patent
Rider

(10) Patent No.: US 9,921,158 B2
(45) Date of Patent: Mar. 20, 2018

(54) METHOD AND APPARATUS FOR DETERMINING ISOTOPIC PROPERTIES OF A SAMPLE MASS

(71) Applicant: BWXT Nuclear Operations Group, Inc., Lynchburg, VA (US)

(72) Inventor: Keith B. Rider, Prospect, VA (US)

(73) Assignee: BWXT Nuclear Operations Group, Inc., Lynchburg, VA (US)

( * ) Notice: Subject to any disclaimer, the term of this patent is extended or adjusted under 35 U.S.C. 154(b) by 259 days.

(21) Appl. No.: 14/978,941

(22) Filed: Dec. 22, 2015

(65) Prior Publication Data

US 2017/0176333 A1 Jun. 22, 2017

(51) Int. Cl.
G01N 21/64 (2006.01)
G01N 23/00 (2006.01)

(52) U.S. Cl.
CPC ....... *G01N 21/6428* (2013.01); *G01N 23/005* (2013.01)

(58) Field of Classification Search
CPC .......... G01N 21/6428; G01N 23/005
See application file for complete search history.

(56) References Cited

U.S. PATENT DOCUMENTS

| | | | |
|---|---|---|---|
| 3,663,815 A | 5/1972 | Cross et al. | |
| 4,900,935 A | 2/1990 | Roberts et al. | |
| 4,925,298 A | 5/1990 | Dobrilla | |
| 4,975,574 A * | 12/1990 | Lucas | G01T 1/178 250/253 |
| 5,087,407 A * | 2/1992 | Gold | G01T 5/10 250/390.04 |
| 5,267,274 A * | 11/1993 | Donelick | G01N 33/24 250/253 |
| 6,459,747 B1 | 10/2002 | van Geel et al. | |
| 9,213,106 B2 | 12/2015 | Miller | |
| 9,229,116 B2 | 1/2016 | Huston et al. | |

(Continued)

FOREIGN PATENT DOCUMENTS

CN 104236978 A 12/2014
WO 2008011674 A1 1/2008

OTHER PUBLICATIONS

Ahmed, M.F., et al., "Comparison between different readout approaches for aluminum oxide radiophotoluminescent crystals," Radiation Measurements 56 (2013), all enclosed pages cited.

(Continued)

*Primary Examiner* — David Porta
*Assistant Examiner* — Djura Malevic
(74) *Attorney, Agent, or Firm* — Nelson Mullins Riley & Scarborough LLP

(57) ABSTRACT

A method and apparatus are provided for determining an isotopic property of a sample mass including placing a sample mass on a solid state detector exposing the solid state detector to a neutron flux. The solid state detector is configured to receive fluorescence damage in response to interaction with a fission product produced from fission of at least a portion of the sample mass. The method also including exposing the solid state detector to a light source, measuring the light emissions of the fluorescence damage, and determining an isotopic property of the sample mass based on the light emissions of the fluorescence damage.

20 Claims, 3 Drawing Sheets

(56) References Cited

U.S. PATENT DOCUMENTS

2010/0327171 A1* 12/2010 Robinson .......... G01T 3/08
250/370.05

OTHER PUBLICATIONS

Akselrod, G.M., et al., "A novel Al2O3 fluorescent nuclear track detector for heavy charged particles and neutrons," Nuclear Instruments and Methods in Physics Research B 247 (2006), all enclosed pages cited.

Akselrod, M.S., et al., "Fluorescent aluminum oxide crystals for volumetric optical data storage and imaging applications," Journal of Fluorescence, vol. 13, No. 6, Nov. 2003, all enclosed pages cited.

Akselrod, M.S., et al., "Fluorescent nuclear track detector technology—a new way to do passive solid state dosimetry," Radiation Measurements 46 (2011), all enclosed pages cited.

Akselrod, M.S., et al., "FNTD radiation dosimetry system enhanced with dual-color wide-field imaging," Radiation Measurements 71 (2014), all enclosed pages cited.

Bartz, J.A., et al., "An imaging spectrometer based on high resolution microscopy of fluorescent aluminum oxide crystal detectors," Radiation Measurements 56 (2013), all enclosed pages cited.

Bartz, J.A., et al., "High resolution charge spectroscopy of heavy ions with FNTD technology," Nuclear Instruments and Methods in Physics Research B 335 (2014), all enclosed pages cited.

Bartz, J.A., et al., "Imaging and dosimetry of synchrotron microbeam with aluminum oxide fluorescent detectors," Radiation Measurements 46 (2011), all enclosed pages cited.

Bondareva, L., "The relationship of mineral and geochemical composition to artificial radionuclide partitioning in Yenisei river sediments downstream from Krasnoyarsk," Environ Monit Assess (2012), all enclosed pages cited.

Charles, M.W., et al., "Hot particle dosimetry and radiobiology—past and present," J. Radiol. Prot. 27 (2007), all inclosed pages cited.

Cheezum, M.K., et al., "Quantitative comparison of algorithms for tracking single fluorescent particles," Biophysical Journal, vol. 81, Oct. 2001, all enclosed pages cited.

Eller, S.A., et al., "Radiophotoluminescence properties of Al2O3:C, Mg crystals," Radiation Measurements 56 (2013), all enclosed pages cited.

Entwistle, J.A., et al., "Identification and characterization of radioactive 'hot' particles in Chernobyl fallout-contaminated soils: the application of two novel approaches," Mineralogical Magazine, Apr. 2003, vol. 67(2), all enclosed pages cited.

Fews, A.P., et al., "High resolution alpha-particle spectroscopy using CR-39 Plastic Track Detector," Nuclear Instruments and Methods in Physics Research (1984), all enclosed pages cited.

Gibson, S.F., et al., "Experimental test of an analytical model of aberration in an oil-immersion objective lens used in three-dimensional light microscopy," J. Opt.Soc.Am.A, vol. 9, No. 1, Jan. 1992, all enclosed pages cited.

Hess, S.T., et al., "Ultra-high resolution imaging by fluorescence photoactivation localization microscopy," Biophysical Journal vol. 91, Dec. 2006, all enclosed pages cited.

Klimpi, G., et al., "Ion range measurements using fluorescent nuclear track detectors," Radiation Measurements 56 (2013), all enclosed pages cited.

Kurobori, T., et al., Time-resolved dose evaluation in an X- and gamma-ray irradiated silver-activated glass detector for three-dimensional imaging applications, Nuclear Instruments and Methods in Physics Research A 793 (2015), all enclosed pages cited.

Lee, M.H., et al., "Investigation on the nuclear track techniques for the screening of the fissile nuclides in swipe samples," Radiation Measurements 46 (2011), all enclosed pages cited.

Niklas, M., et al., "Engineering cell-fluorescent ion track hybrid detectors," Radiation Oncology 8:141 (2013), all enclosed pages cited.

Niklas, M., et al., "Ion track reconstruction in 3D using alumina-based fluorescent nuclear track detectors," printed from physics.med-ph, Jun. 10, 2013, all enclosed pages cited.

Niklas, M., et al., "Spatial Correlation between traversal and cellular response in ion radiotherapy—towards single track spectroscopy," Radiation Measurements 56 (2013), all enclosed pages cited.

Osinga, J., "Fluorescent nuclear track detectors: High-Accuracy fluence determination in ion beams," Martin Luther University of Halle—Wittenberg, Oct. 15, 2012, all enclosed pages cited.

Osinga, J., et al., "High accuracy fluence determination in ion beams using fluorescent nuclear track detectors," Radiation Measurements 56 (2013), all enclosed pages cited.

Osinga, J., et al., "Single track coincidence measurements of fluorescent and plastic nuclear track detectors in therapeutic carbon beams," IOP Publishing, Apr. 15, 2014, all enclosed pages cited.

Peräjärvi, K., et al., "Determination of 235U, 239Pu, 240Pu, and 241Am in a Nuclear Bomb Particle using a position-sensitive α-γ coincidence technique," Environmental Science and Technology, Jan. 19, 2011, all enclosed pages cited.

Solon, E., et al., "Autoradiography, MALDI-MS, and SIMS-MS imaging in pharmaceutical discovery and development," The AAPS Journal, vol. 12, No. 1, Mar. 2010, all enclosed pages cited.

Sykora, G., et al., "Novel fluorescent nuclear track detector technology for mixed neutron-gamma fields," Radiation Measurements 45 (2010), all enclosed pages cited.

Sykora, G., et al., "Properties of novel fluorescent nuclear track detectors for use in passive neutron dosimetry," Radiation Measurements 43 (2008), all enclosed pages cited.

Thompson, R., et al., "Precise nanometer localization analysis for individual fluorescent probes," Biophysical Journal, vol. 82, May 2002, all enclosed pages cited.

Zeissler, C., et al., "Spectral measurements of imaging plate backgrounds, alpha-particles and beta-particles," Nuclear Instruments and Methods in Physics Research A 624 (2010), all enclosed pages cited.

Petford, N. and Miller, J.A., "Three-Dimensional Imaging of Fission Tracks Using Confocal Scanning Laser Microscopy", American Mineralogist, vol. 77, pp. 529-533 (1992).

Young, D.A.: 'Etching of Radiation Damage in Lithium Fluoride', Nature, vol. 182, Issue 4632, Aug. 1958, p. 375-377.

Smith, M.J., 'Automated Microscope Scanning Stage for Fission-Track Dating', Nuclear Tracks, vol. 10, No. 3, 1985, p. 395-400.

Montereali, R.M., et al., "F and F-aggregates colour centres in lithium fluoride for high spatial resolution x-ray imaging," Journal of Physics: Conference Series 249 (2010), all enclosed pages cited.

* cited by examiner

METHOD AND APPARATUS FOR DETERMINING ISOTOPIC PROPERTIES OF A SAMPLE MASS

TECHNICAL FIELD

Example embodiments generally relate to detection of fissionable material and, in particular, relate to a method and apparatus for determining isotopic properties of a fissionable sample mass.

BACKGROUND

Fission track analysis is a traditional method for locating fissionable material mixed with large amounts of inert material. In a conventional method of fission track analysis, a sample, e.g. a micron size sample mass, may be placed on a plastic or mica detector material and exposed to a neutron flux from a nuclear reactor. Neutron absorption of fissionable material causes fission reactions that produce fission products, in particular energetic heavy ions, that may penetrate into the detector material. The penetration of the fission products into the detector material may cause an ionization trail of damaged material, or a latent fission track.

The fission tracks may be enlarged by chemical etching to produce a visible defect which can be imaged using an optical microscope. The appearance of fission tacks near fissionable material may be used to distinguish fissionable material from inert material, which do not produce such tracks. Further, fission tacks identified by microscopic examination may be subjectively compared to known fission track patterns to determine a likely isotope and/or enrichment of the sample mass.

Additionally or alternatively, sample masses may undergo elemental or isotopic analysis, such as by mass spectrometry. These analyses may require scarce, highly sensitive, and/or highly expensive equipment.

This process may require a considerable amount of time to determine the isotopes and enrichment level thereof within the samples, in some instances twenty days or more. Additionally, this method requires large non-transportable or very expensive equipment, such as a nuclear reactor and/or a mass spectrometer. The scarcity of the equipment and distances from sample points may cause increased cost of analysis and require substantial sample transit time.

BRIEF SUMMARY OF SOME EXAMPLES

Accordingly, some example embodiments may enable the determination of an isotopic property of a sample mass, as described below. In one example embodiment, a method for determining an isotopic property of a sample mass is provided, including placing a sample mass on a solid state detector, and exposing the solid state detector to a neutron flux. The solid state detector is configured to receive fluorescence damage in response to interaction with a fission product produced from fission of at least a portion of the sample mass. The method also includes exposing the solid state detector to a light source, measuring light emissions of the fluorescence damage, and determining an isotopic property of the sample mass based on the light emissions of the fluorescence damage.

In another embodiment, a method for determining an isotopic property of a sample mass is provided, including enclosing the sample mass between a first solid state detector and a second solid state detector and exposing the solid state detector to a neutron flux. The solid state detector is configured to receive fluorescence damage in response to interaction with a fission product produced from fission of at least a portion of the sample mass. The method also includes exposing the solid state detector to a light source at a first wavelength, measuring light emissions of the fluorescence damage at a second wavelength, and determining an isotopic property of the sample mass based on light emissions of the fluorescence damage.

In yet another example embodiment, a solid state detector is provided, including a sample surface configured to receive a sample mass. The solid state detector is configured to receive fluorescence damage in response to interaction with a fission product produced from fission of at least a portion of the sample mass.

BRIEF DESCRIPTION OF THE SEVERAL VIEWS OF THE DRAWING(S)

Having thus described the method and apparatus in general terms, reference will now be made to the accompanying drawings, which are not necessarily drawn to scale, and wherein:

DETAILED DESCRIPTION

Figure 1:
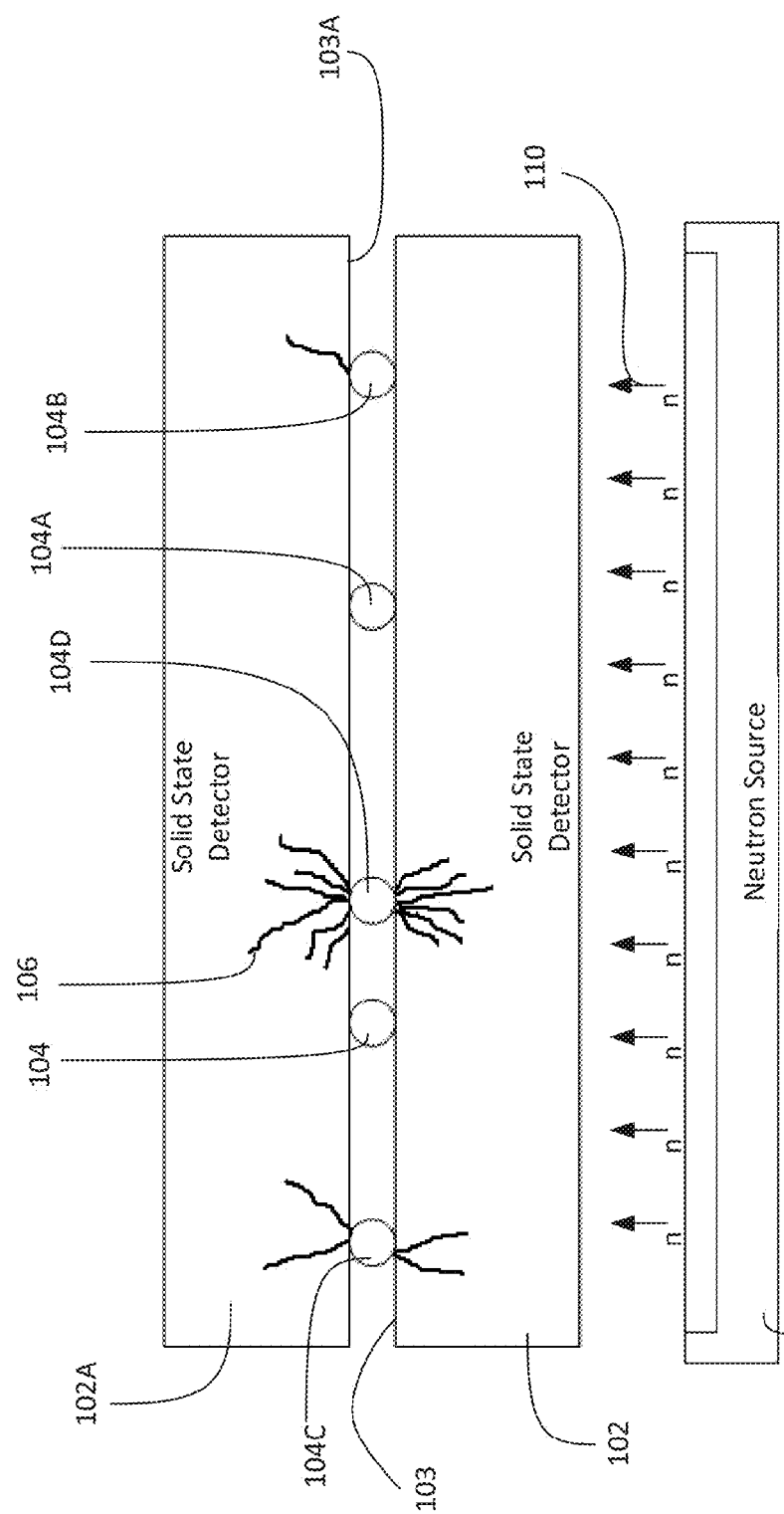
FIG. 1 illustrates an example block solid state detector according to an example embodiment.

Some example embodiments now will be described more fully hereinafter with reference to the accompanying drawings, in which some, but not all, example embodiments are shown. Indeed, the examples described and pictured herein should not be construed as being limiting as to the scope, applicability, or configuration of the present disclosure. It will be apparent to those skilled in the art that modifications and variations can be made in such example embodiments without departing from the scope or spirit thereof. For instance, features illustrated or described in one embodiment may be used on another embodiment to yield a still further embodiment. Thus, it is intended that the present invention covers such modifications and variations as come within the scope of the appended claims and their equivalents.

With regard to the description within the present disclosure as it addresses the drawings, like reference numerals refer to like elements throughout. As used herein, "operable coupling" should be understood to relate to direct or indirect connection that, in either case, enables functional interconnection of components that are operably coupled to each other.

Further, the term "or" as used in this application and the appended claims is intended to mean an inclusive "or" rather than an exclusive "or." That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be understood to mean "one or more" unless specified otherwise or clear from the context to be directed to a singular form. Throughout the specification and claims, the following terms take at least the meanings explicitly associated therein, unless the context dictates otherwise. The meanings identified below do not necessarily limit the terms, but merely provide illustrative examples for the terms. The meaning of "a," "an," and "the" may include plural references, and the meaning of "in" may include "in" and "on." The phrase "in one embodiment" or other similar phrase, as used herein, does not necessarily refer to the same embodiment, although it may.

In an example embodiment, a solid state detector may be provided on which a sample mass may be placed. In some example embodiments, a second solid state detector may be provided and the sample mass enclosed between the first solid state detector and the second solid state detector. The solid state detector may be exposed to a neutron flux, such as can be generated by a neutron generator. The solid state detector may receive fluorescence damage in response to interaction with a fission product of at least a portion of the sample mass.

The solid state detector may be exposed to a light source, such as a laser, at a certain, predetermined wavelength. In response to the exposure to the light source at a first wavelength, the fluorescence damage of the solid state detractor may emit or refract light of a second wavelength. A fluorescence intensity and sample volume may be determined for each instance of fluorescence damage, e.g. ionization tracks, such as fission tracks and alpha particle tracks, associated with a given sample mass. The ionization tracks may include a plurality of Farbe center, e.g. F center, defects, in some instances thousands of F center defects. A ratio of the so-determined fluorescence intensity to the determined sample volume is compared to known intensity/volume ratios to determine an isotopic property, such as the identity of the isotope that creates the florescence damage and/or the enrichment level of the sample mass. A quantitative determination of the isotope and/or enrichment level may be determined based on the comparison of the determined and known intensity/volume ratios.

In some embodiments, a coordinate position of the sample mass, following the detector's exposure to the neutron flux and creation of the florescence damage, may be determined within a predetermined two or three dimensional reference system that is correlated to the solid state detector. The sample mass may be efficiently removed from the solid state detector by manual or robotic particle removal and undergo further elemental or isotopic analysis, such as by mass spectrometry.

In some example embodiments, the solid state detector may be an optically transparent salt crystal such as lithium fluoride. The fluorescence damage may be crystal matrix defects caused by interaction with fission products of fissionable material in the sample mass.

In an example embodiment, all equipment used in the analysis, e.g. the neutron generator, light source and light equipment, may be portable, thereby allowing for determinations to be made on site where the sample material is collected. Further, the process may be significantly more efficient than traditional processes since the detector does not need to undergo chemical etching or require nuclear reactor operations. In some instances, the process may produce results in the same day in which the sample is taken, which may be beneficial in applications, such as nuclear weapons inspections, in which time is of the essence. The optical, e.g. fluorescence, analysis may additionally be more sensitive than traditional methods, permitting a lower neutron flux to be employed. The lower neutron flux may allow portable neutron sources to be utilized.

Example Solid State Detector

An example embodiment of the method and apparatus will now be described with reference to FIG. 1, which illustrates an example solid state detector 102. Solid state detector 102 may be a salt crystal, polymer, inorganic crystal, natural mineral, or the like. In an example embodiment in which solid state detector 102 is a salt crystal, the salt crystal may be lithium fluoride, calcium fluoride, calcium sulfate, lithium bromide, calcium borate, potassium bromide, feldspar, or the like. In an example embodiment, the salt crystal may optionally be doped with an impurity in order to enhance the crystal's stability at a desired temperature range, enhance the fluorescence effect, or possibly other purposes, such as magnesium, titanium, silver, dysprosium, europium, or the like As should be understood, the crystal structure reconstructs at or above a temperature, which may be referred to as the annealing temperature, that depends on the crystal material's composition. If solid state detector 102 in which fission tracks have been formed is maintained at a temperature above its annealing temperature, the crystal structure may partially or entirely repair the tracks, thereby inhibiting or prohibiting the tracks' detection. Accordingly, in presently described embodiments, solid state detector 102 may comprise a detector material having a (doped or non-doped) crystal structure that is stable with and/or without defects at temperatures within the temperature range the detector is expected to experience during the detection process and post-process handling and analysis. That is, the detector material has an annealing temperature, e.g. at least 100 degrees Celsius or thereabout, that is above the detector's normal operating temperature range. In an example embodiment in which the salt crystal is lithium fluoride, the crystal matrix defects may be stable, e.g. not repair or anneal, at temperatures up to and including 100 degrees Celsius and may anneal where the crystal is heated to 250-300 degree Celsius. A longer period of heat exposure may be needed to anneal defects at lower temperatures within the anneal band. The stability of the crystal matrix may be beneficial in hot environments, such as the dessert, nuclear flux exposure, or the like, and it is anticipated by the present disclosure that a detector material may be chosen for a given detector at least in part based on the expected temperature range in which the detector may be used.

The defects in the crystal structure caused by fission product interactions have the characteristic of fluorescence and may, therefore, be considered fluorescence damage. These defects, e.g. F centers, when exposed to a light source of a first coherent or peak wavelength, may fluoresce, i.e. emit or refract light, at a second peak wavelength that is offset from the first wavelength. The composition of the solid state detector 102 material, and thus the selection of the material of which detector 102 is formed, dictates the first and second wavelengths. The light source and fluorescence wavelengths for solid state detector materials may be predetermined, so that a confocal microscope system, or other optical analysis system, used to detect the defects may be set to excite the solid state detector 102 substrate(s) with light at the first wavelength but detect light at the second wavelength, according to the known characteristics of the substrate material. As a result of the difference between the excitation wavelength and the emission wavelength, the confocal microscope may filter the excitation wavelength in its detection stage, thereby allowing detection of the fluorescence without interference from the excitation light.

Solid state detector 102 may include a sample surface 103 that receives a sample mass 104, such as a sample mass of atoms having a size on an approximately micron scale. A sample may be collected by a swipe of a surface, such as at a nuclear processing facility, where there exists a suspected or possible presence of fissionable material. The sample may include one or more sample masses 104. The sample masses may include fissionable material 104B, 104C, 104D, and/or inert material 104A. The fissionable material may be Uranium 235, Uranium 238, or transuranic elements.

The sample masses 104 may be removed from the surface swipe, e.g. made with a porous material such as cloth, and placed on sample side 103 of solid state detector 102. The sample masses may be removed from the swipe and deposited on side 103 by stretching or liquid submersion and application of ultrasonic agitation. In some instances, an adhesive may be applied to the sample surface 103, 103A to thereby adhere the sample masses 104 to the sample surface 103, 103A. In one example embodiment, sample masses 104 may be adhered to the sample surface using a collodion, such as four-to-eight percent cellulose nitrate in a mixture of ethanol and ether.

In an example embodiment, a second solid state detector 102A may enclose the sample masses 104 between the sample surface 103 of the first solid state detector 102 and the sample surface 103A of the second solid state detector 102A.

The solid state detector 102 may be exposed to a neutron source 108, such as a radioactive neutron source, neutron generator, or nuclear reactor. The neutron flux may be sufficient to induce fission of uranium atoms of the sample mass. In some example embodiments, the neutron source 108 may have a neutron flux 110 of about $10^{12}$ n/cm$^2$/s. The duration of the exposure to the neutron source 108 maybe a predetermined amount of time. The duration of the exposure of the solid state detector 102 to the neutron flux 110 may be selected through testing to achieve a desired fission response of uranium atoms, to thereby create a desired, or expected, fission track pattern, depending on the type of fissionable material that may be present in the sample mass 104. For example, the exposure time may be sufficient to cause fission of atoms of at least one uranium atom of the sample mass, if present, within a mass of a large size within the expected size range and enrichment range of the sample mass. Longer exposure may result in fission of smaller sample masses 104 and/or of sample masses having lower enrichment levels. Accordingly, as will be apparent from the present disclosure, an increased exposure time increases the ability to detect a wider range of isotopes, but it also increases the likelihood of reduced accuracy of analysis caused by fission track overlap. The depth and/or number of fission tracks may be dependent on, e.g. proportional to, the intensity and duration of the neutron flux 110 exposure.

Neutron interactions with inert sample masses 104A do not cause fission within those masses and therefore will create no resultant damage to the crystal structure of the solid state detector 102. Neutron interactions with fissionable sample masses 104B, 104C, 104D may cause fluorescence damage 106 to the crystal matrix of the solid state detector 102. The fluorescence damage 106 may be a crystal defect, or F-center, that is stable in the crystal matrix. Fluorescence damage 106 may be a fission ionization trail or track caused by the penetration of a fission product of a fission of one or more atoms of the fissionable sample mass 104B, 104C, 104D. The fission products may include heavy ions, such as Cesium-137, Strontium-90, or the like. In some example embodiments, the fission product may be an alpha particle, which may be useful for transuranic isotope detection or differentiation. The depth and/or number of fission tracks of each instance of fluorescence damage 106 may be indicative of the isotope and/or enrichment level of the fissionable material in the sample mass 104 exposed to a known neutron flux 110 intensity and duration. As discussed above, an inert sample mass 104A may not undergo fission, and therefore not cause fluorescence damage to the solid state detector 102, 102A. A fissionable sample mass containing naturally occurring uranium, e.g. about 99 percent Uruanium-238 and <1 percent Uranium 235, may cause fluorescence damage 106 having few fission tracks. A fissionable sample mass containing low enriched uranium 104C, e.g. about 95-98 percent Uranium-238 and two-to-five percent Uranium-235, may cause fluorescence damage 106 having more fission tracks 106 with deeper penetration into the solid state detector 102, 102A than would be caused by naturally occurring uranium sample masses 104B. Sample masses containing highly enriched uranium 104D, e.g. about ten-to-twenty percent Uranium 238 and eighty-to-ninety or greater percent Uranium 235, may cause fluorescence damage 106 having more fission tracks 106 in the solid state detector 102, 102A than would be caused by low enriched uranium sample masses 104C. In some instances, transuranic elements, such as plutonium, may also be present in highly enriched sample masses 104D.

Example Solid State Detector Exposure to Light Source

Figure 2:
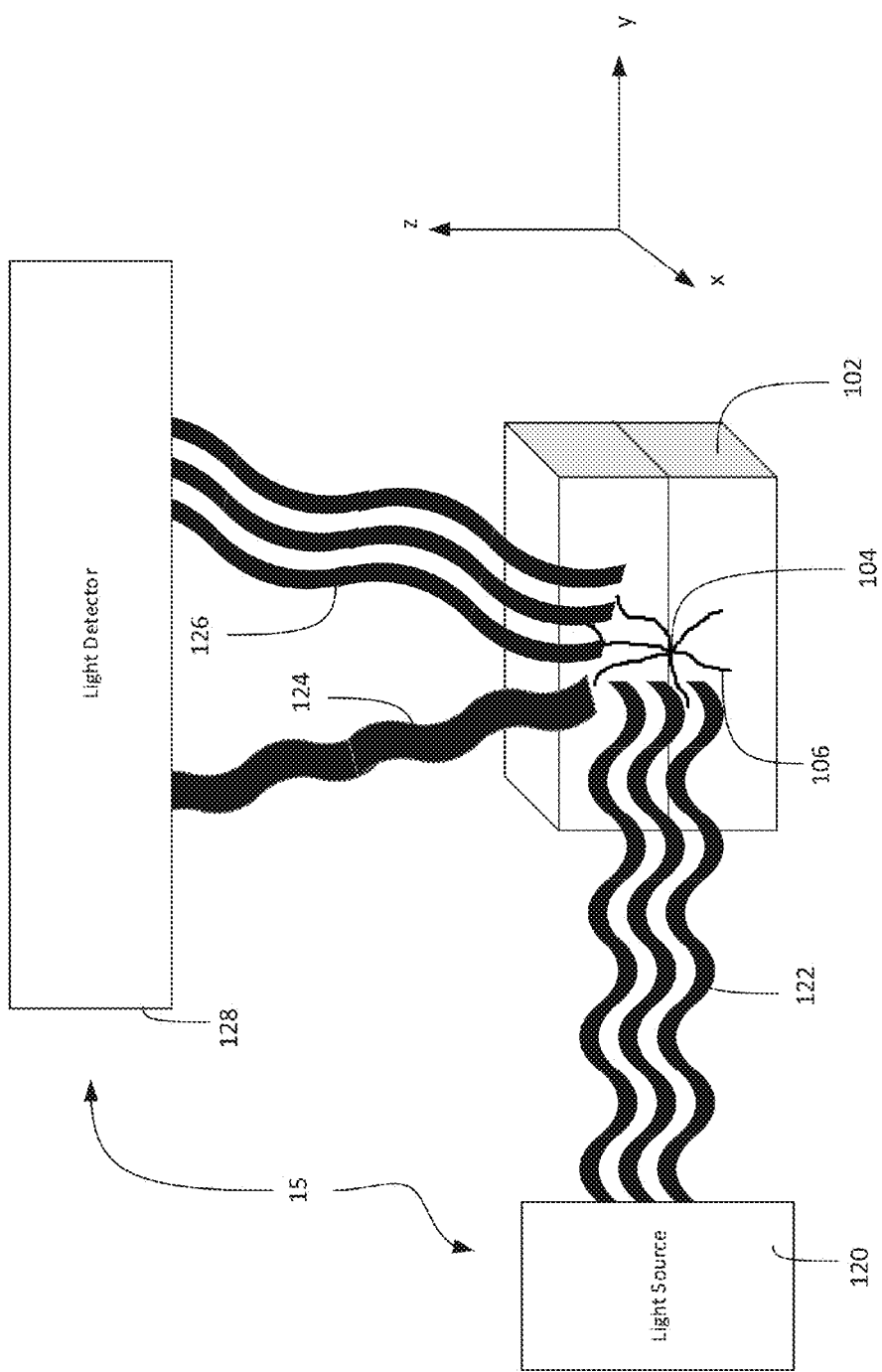
FIG. 2 illustrates an example solid state detector exposure to a light source according to an example embodiment.

FIG. 2 illustrates an example solid state detector exposure to a light source according to an example embodiment. Solid state detector 102 may undergo the sample mass placement and exposure to the neutron source 108 as discussed above with respect to FIG. 1. Solid state detector 102 may next undergo confocal fluorescence microscopy, such as confocal laser scanning microscopy. A confocal fluorescence microscope 15 may include a light source 120 and a light detector 128. Solid state detector 102 may be exposed to the light source 120, such as an argon laser, at a first coherent or peak wavelength 122, such as 458 nm in the case of a lithium fluoride solid state detector 102. Fluorescence damage 106, e.g. the F-centers, refract or emit light, i.e. fluoresce, at a second peak wavelength 126 in response to excitation light from light source 120. In an instance in which solid state detector 102 is made of lithium fluoride as the substrate material, fluorescence damage 106 may emit light a wavelength of 535 nm and/or 670 nm. In some example embodiments, light of other wavelengths may be used in addition to light of the first wavelength (which causes emission of light at the second wavelength); for example light source 120 may emit light of a third wavelength causing fluorescence damage 106 to emit light (detected by light detector 128) at a fourth wavelength that is different from the third wavelength.

Light detector 128, such as a spectrometer, one or more photon detectors, photomultipliers, or the like, may measure the intensity of the fluorescent light emissions 124 from the fluorescence damage at the second wavelength. In some embodiments, a filter may limit or prevent light of wavelengths other than the second wavelength 124 from entering and/or being detected by the light detector 128. In an example embodiment, a fluorescence intensity background measurement may be taken in an undamaged area and subtracted from the measurement taken at or near the fluorescence damage 106, in order to increase sensitivity of the measurements. The light detector may determine a fluorescence intensity based on the measured light emissions 126 of the fluorescence damage 106. In an example embodiment, a field of view of the light detector 128 may be selected that encompasses light emitted by fluorescence damage 106 associated with one sample mass 104. The fluorescence intensities of the second wavelength 126 associated with the ionization or fission tracks of fluorescence damage 106 may be summed to quantify the fluorescence intensity for the sample mass 104. Additionally or alternatively, a fluorescence intensity profile may be generated based on florescence damage 106 through use of the confocal microscope system. As should be understood, confocal microscopes can identify light intensity not only in a two-dimensional focal plane perpendicular to the microscope's optical axis, but also in terms of depth parallel to the optical axis. Thus, the confocal microscope system can record data identifying light intensity as a function of a two-dimensional or three-dimensional space, thereby defining profiles of florescence damages 106 within the predefined space. The shape and depth of the florescence damage 106 ionization tracks may be measured for the sample mass 104. Track profiles may, for example, aid in determining sample properties. For example, florescence damage 106 associated with an alpha particle may produce tracks that are relatively shallow compared to fission tracks. The alpha tracks may also have a shape that is distinct from fission track florescence damage 106.

In some example embodiments, the volume of a sample mass 104 may be determined based on an optical microscope image. The volume of the sample mass may be determined based on the number of pixels the sample mass 104 occupies in the image. Through calibration testing, the user may determine how much area of a target surface corresponds to each pixel in a microscope image for a given optical microscope under the same conditions at which the detector is examined. Accordingly, identification of the sample mass 104 in the optical microscope image, and in particular the number of pixels occupied by the sample mass 104 in the image, identifies the area of the sample mass 104 outermost perimeter in the microscope's focal plane. If images are available from multiple angles, so that perimeter areas can be obtained in orthogonal or otherwise transverse planes, the sample volume may be estimated from assumptions of the three dimensional shape of the sample mass 104 based on the perimeter sections. If only a single view is available, a three dimensional shape of the sample mass 104 may be assumed from knowledge of typical sample mass formations and the one available perimeter, with the volume then being definable by integrating the perimeter area information over the assumed volume. Additionally or alternatively, the volume of the sample mass 104 may be determined based on three dimensional mapping. In an example embodiment, a three dimensional map of the sample mass 104 may be generated by a confocal microscope. The confocal microscope may measure the reflectance at a light detector 128 of the sample mass 104 exposed to light emissions from the light source 120. The light emissions and detected reflectance may be the same wavelength or the first wavelength 122 and second wavelength 124, as discussed above.

An intensity/volume ratio may be the integrated fluorescence intensity of the particular fluorescence damage 106 divided by the volume of the sample mass 104. For example, where an integrated fluorescence intensity of a fluorescence damage 106 may be XXX and the volume of the sample mass may be YYY, the specific fluorescence intensity is XXX/YYY=ZZZ.

In some example embodiments, the determined intensity/volume ratio of the fluorescence damage 106 may be compared to one or more known intensity/volume ratios, for example intensity/volume ratios of naturally occurring uranium, low enriched uranium, such as three percent enrichment, and high enriched uranium, such as ninety percent, or the like. The intensity/volume ratios may correspond to solid state detectors 102 and sample masses 104 that have undergone neutron flux 110 of substantially similar magnitude and duration. That is, the known ratios, for each given uranium type, are defined for a given neutron flux magnitude and duration. Accordingly, prior to execution of an analysis as described herein, these known ratios may be determined through calibration by placing a sample mass of known fissionable material upon respective detector substrates of the same materials and dimensions that will be used in later sample testing, applying a neutron flux to such calibration sample at a magnitude and duration that will be used in the later sample testing, determining the fluorescence intensity as described above, applying the first wavelength light to the calibration sample mass, measuring the florescence intensity of the fluorescence damage 106, determining the sample mass volume as described above, determining the fluorescence intensity/mass volume ratio as described above, and repeating this process for each uranium type, for each detector substrate material, and for each neutron flux magnitude and duration expected during such testing. Thus, when a test is made using a given detector substrate at a given neutron flux magnitude and duration, the resulting intensity/volume ratio may be compared to the calibrated intensity/volume ratios acquired for the same detector substrate material, neutron flux magnitude, and neutron flux duration, thereby allowing identification of the isotope by determining which of the resulting calibration ratios is closest to the ratio(s) determined from the test. In an example embodiment, the total fluorescent damage in the solid state detector 102 around a sample mass 104 is quantifiable. For a given isotope, sample mass 104 size, neutron flux 110, and illumination intensity, the fluorescent yield is proportional to the fissionable isotope concentration. The proportional values may be represented in a formula that allows the operator to input all the variables to calculate the fissionable isotope concentration, or represented in a quick-reference chart.

Additionally or alternatively, and as noted above, a florescence intensity profile may be generated for the calibrated sample masses. The florescence intensity profile may include the shape and depth of the florescence damage 106 cause by alpha particles and/or fission, which may be useful in differentiating transuranic isotopes, such as plutonium.

One or more isotopic properties of the sample mass 104 may be determined based on the comparison of the determined intensity/volume ratio and the known intensity/volume ratios. Isotopic properties may include identification of the isotope or isotopes that have undergone fission, the uranium enrichment level, or the like. In an example embodiment, the isotopic properties may be determined as the isotopic properties associated with the closest known intensity/volume ratio to the determined intensity/volume ratio. In some embodiments, the isotopic properties may be identified by an interpolation between isotopic properties associated with the two or more known intensity/volume ratios and the determined intensity volume ratio. For example, the isotopic properties of a sample mass may be 99 percent Uranium 238, indicating naturally occurring uranium; 4 percent Uranium-235, 96 percent Uranium 238, indicative of nuclear power application enrichment levels; 85 percent Uranium 235 and 15 percent Uranium 235, indicative of nuclear weapons applications, or the like.

Additionally or alternatively, the isotopic properties of the sample mass 104 may be determined based on a florescence intensity profile. In an example embodiment, a florescence intensity profile for the sample mass 104 may be compared to a florescence profile of a calibrated sample mass.

In some example embodiments, as noted above, the confocal fluorescence microscopy may include a determination of the location of sample mass 104 within solid state detector 102. The determination of the location sample mass may be a two dimensional coordinate, such as an x,y coordinate of sample surface 103, 103A. Additionally or alternatively, the location of sample mass 104 may be a three dimensional coordinate, such as an x,y,z coordinate, defined for and situated within or upon solid state detector 102, 102A. Accordingly, in an example embodiment, the confocal microcopy may output a three dimensional image of the solid state detector 102 or a series of two dimensional images on different focal planes. The solid state detector may include one or more fiducial marks. The two dimensional or three dimensional coordinate location may be determined based on the position of the sample mass 104 relative to one or more of the fiducial marks in the three dimensional image or two dimensional images.

The determination of isotopic properties based on fluorescence damage, as discussed above, may allow for on site or near site analysis of sample masses 104 in a relatively short period, such as in the order of hours, due to the portability and durability of solid state detector 102 and analysis equipment. Solid state detector 102 and the analysis equipment may also be of a cost that is not prohibitive for an agency, company or the like to acquire a sufficient number to equip more than one mobile inspection team, thereby reducing or eliminating the need to ship samples to a testing facility. Additionally, the determination of isotopic properties based on fluorescence damage is non-destructive to the sample, allowing for additional testing and conformation of the isotopic properties of the sample masses.

In an embodiment, for example, sample mass 104 may be removed from solid state detector 102, 102A, such as by tweezers on a micropositioner. The micropositioner may utilize the determined sample mass location, e.g. coordinate position, as discussed above, to target the removal of the sample mass 104.

Sample mass 104 may undergo further isotopic analysis, such as mass spectrometry. In an example embodiment, sample mass 104 may be placed on a sample wire and entered into a mass spectrometer. The mass spectrometry may provide a confirmation of the isotopic properties of sample mass 104 determined by the confocal microscopy procedure and/or additional isotopic property information, such as the isotopic makeup of each tested sample mass 104. The number of sample masses that may under go mass spectrometry to locate fissionable material may be significantly reduced, since isotopic properties for the sample masses may be known based on the florescence damage.

Method for Determining an Isotopic Property of a Sample Mass

Figure 3:
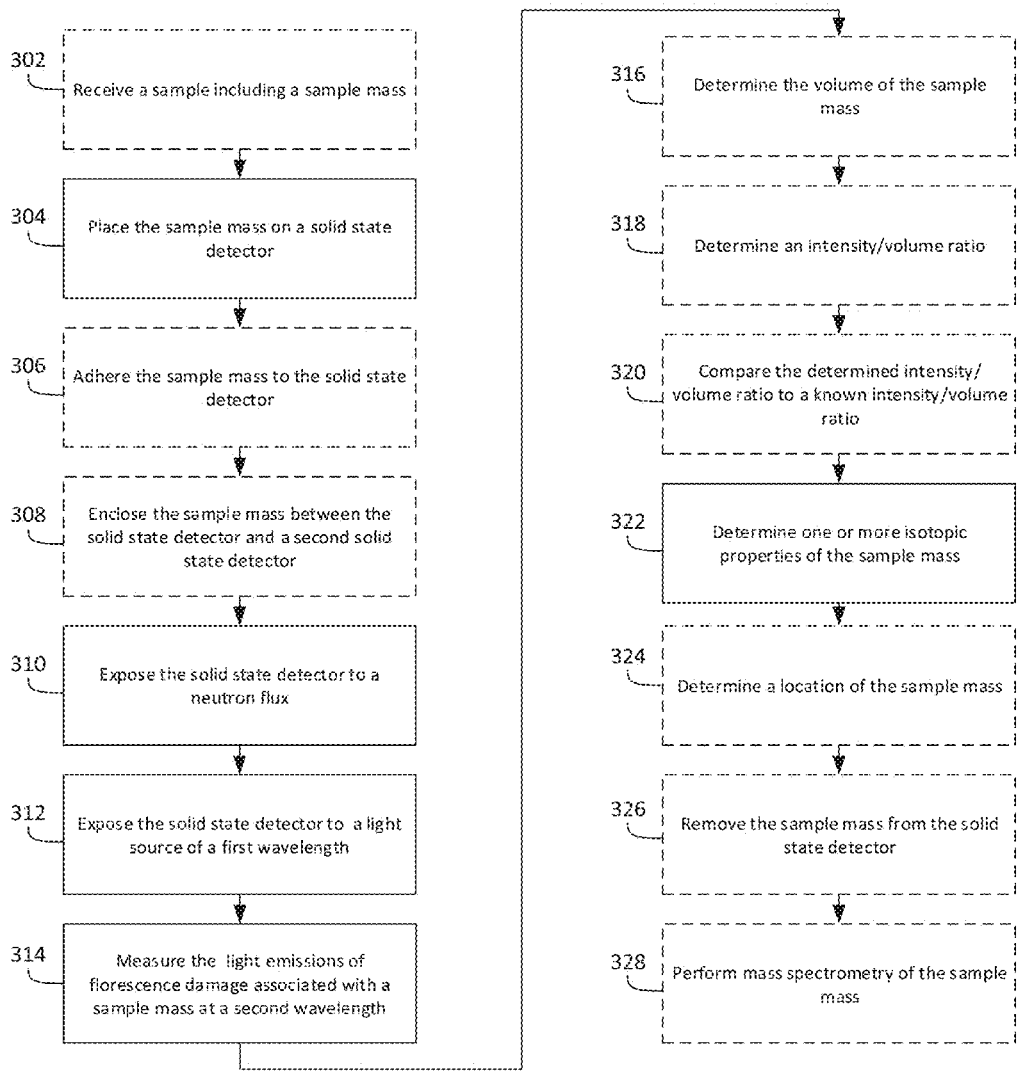
FIG. 3 illustrates an example flowchart of a method for determining an isotopic property of a sample mass according to an example embodiment.

FIG. 3 illustrates an example flowchart of a method for determining an isotopic property of a sample mass according to an example embodiment. The method may include, at operation 304, placing a sample mass 104 on a solid state detector 102. At operation 310, the method may include exposing solid state detector 102 to a neutron flux 110. The method may include exposing solid state detector 102 to a light source 120 at a first wavelength, at operation 312, and measuring the light emissions of fluorescence damage 106 associated with a sample mass 104 at a second wavelength, at operation 314. The method may also include determining one or more isotopic properties of the sample mass, at operation 322.

In an example embodiment, the method may optionally include, as denoted by the dashed box, operation 302, receiving a sample including a sample mass 104. The method may also optionally include adhering the sample mass to the solid state detector 102, at operation 306, or enclosing the sample mass between the solid state detector 102 and a second solid state detector 102A. In some example embodiments, the method may optionally include determining the volume of sample mass 104, at operation 316, determining an intensity/volume ratio, at operation 318, or comparing the determined intensity/volume ratio to a known intensity/volume ratio, at operation 320. In an example embodiment, the method may also include determining a location of the sample mass, at operation 324, removing the sample mass from the solid state detector, at operation 326, or performing mass spectrometry of the sample mass at operation 328.

In some embodiments, the method or apparatus for determining an isotopic property of a sample mass may be configured for further optional modifications. In this regard, for example, the light source radiates light at a first coherent or peak wavelength, and the fluorescence damage fluoresces at a second peak wavelength. In an example embodiment, the method also includes determining a fluorescence intensity based on the measured light emissions of the fluorescence damage associated with the sample mass, determining a sample mass volume, determining an intensity/volume ratio based on the fluorescence intensity and the sample mass volume, and comparing the determined intensity/volume ratio to a known intensity/volume ratio. Determination of the isotopic property of the sample mass is further based on the comparison of the determined intensity/volume ratio and the known intensity/volume ratio. In some example embodiments, the method also includes enclosing the sample mass between the solid state detector and a second solid state detector. In an example embodiment, the method also includes removing the sample mass form the solid state detector and performing mass spectrometry of the sample mass. In some example embodiments, the solid state detector is a salt crystal and the fluorescence damage is a crystal defect. In an example embodiment, the salt crystal is lithium fluoride. In some example embodiments, the solid state detector is optically transparent. In an example embodiment, the method also includes adhering the sample mass to the solid state detector. In some example embodiments, the isotopic property comprises isotope identification of the sample mass. In an example embodiment, the isotopic property further comprises isotope enrichment level. In some example embodiments, at least a portion of the sample mass is uranium oxide. In an example embodiment, the solid state detector crystal material is, and therefore defects therein are, stable at less than 100 degrees Celsius. In some example embodiments, the solid state detector also includes a second solid state detector, and the first solid state detector and second solid state detector are configured to enclose the sample mass between the sample surface of the solid state detector and a sample surface of the second solid state detector. In an example embodiment, the solid state detector is a salt crystal and the fluorescence damage is a crystal defect. In some example embodiments, the salt crystal is lithium fluoride. In an example embodiment, the solid state detector is optically transparent. In some example embodiments, the fluorescence damage emits light at a second peak wavelength in response to exposure of the solid state detector to a light source at a first wavelength.

The method and apparatus for determining an isotopic property of a sample mass, as provided above, allow for determination of the isotopic properties of the sample mass in a substantially shorter period of time, e.g. hours instead of days, than traditional methods. The shortened analysis period may be particularly beneficial in an application, such as a nuclear weapon inspection, in which time is of the essence. Further, the optical, e.g. fluorescence, based analysis may not require sophisticated vacuum systems or delicate instruments, allowing for portability of the analysis equipment. The method may also be more sensitive than the traditional method, thereby allowing for relatively low neutron fluxes to be employed, which in turn permits the use of a portable neutron source or neutron generator instead of the costly and non-portable nuclear reactor.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Moreover, although the foregoing descriptions and the associated drawings describe exemplary embodiments in the context of certain exemplary combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. In cases where advantages, benefits or solutions to problems are described herein, it should be appreciated that such advantages, benefits and/or solutions may be applicable to some example embodiments, but not necessarily all example embodiments. Thus, any advantages, benefits or solutions described herein should not be thought of as being critical, required or essential to all embodiments or to that which is claimed herein. Although specific terms are employed herein, they are used in a generic and descriptive sense only and not for purposes of limitation.

That which is claimed:

1. A method for determining an isotopic property of a sample mass comprising:
   placing a sample mass on a solid state detector;
   exposing the solid state detector to a neutron flux, wherein the solid state detector is configured to receive fluorescence damage in response to interaction with a fission product produced from fission of at least a portion of the sample mass;
   exposing the solid state detector to a light source;
   measuring light emissions of the fluorescence damage in response to the exposure to the light source; and
   determining an isotopic property of the sample mass based on the light emissions of the fluorescence damage.

2. The method of claim 1, wherein the light source is at a first wavelength and the light emissions of the fluorescence damage is at a second wavelength.

3. The method of claim 2 further comprising:
   determining a fluorescence intensity based on the measured light emissions of the fluorescence damage associated with the sample mass;
   determining a sample mass volume;
   determining a intensity/volume ratio based on the fluorescence intensity and the sample mass volume;
   comparing the determined intensity/volume ratio to a known intensity/volume ratio,
   wherein determining the isotopic property of the sample mass is further based on the comparison of the determined intensity/volume ratio and the known intensity/volume ratio.

4. The method of claim 1, further including enclosing the sample mass between the solid state detector and a second solid state detector.

5. The method of claim 1 further comprising:
   removing the sample mass form the solid state detector; and
   performing mass spectrometry of the sample mass.

6. The method of claim 1, wherein the solid state detector comprises a salt crystal and the fluorescence damage comprises a crystal defect.

7. The method of claim 6, wherein the salt crystal comprises lithium fluoride.

8. The method of claim 1, wherein the solid state detector is optically transparent.

9. The method of claim 1 further comprising:
   adhering the sample mass to the solid state detector.

10. The method of claim 1, wherein the isotopic property comprises isotope identification of the sample mass.

11. The method of claim 1, wherein the isotopic property further comprises isotope enrichment level.

12. The method of claim 1 wherein at least a portion of the sample mass is uranium oxide.

13. The method of claim 1, wherein the solid state is crystal defect stable at less than 100 degrees Celsius.

14. A method for determining an isotopic property of a sample mass: comprising:
    enclosing the sample mass between a first solid state detector and a second solid state detector;
    exposing the solid state detector to a neutron flux, wherein the solid state detector is configured to receive fluorescence damage in response to interaction with a fission products produced from fission of at least a portion of the sample mass;
    exposing the solid state detector to a light source at a first wavelength;
    measuring light emissions of the fluorescence damage at a second wavelength in response to the exposure to the light source; and
    determining an isotopic property of the sample mass based on the light emissions of the fluorescence damage.

15. A solid state detector comprising:
    a sample surface configured to receive a sample mass;
    wherein the solid state detector is configured to receive fluorescence damage in response to interaction with a fission product produced from fission of at least a portion of the sample mass.

16. The solid state detector of claim 15 further comprising:
    a second solid state detector,
    wherein the solid state detector and second solid state detector are configured to enclose the sample mass between the sample surface of the solid state detector and a sample surface of the second solid state detector.

17. The solid state detector of claim 15, wherein the solid state detector comprises a salt crystal and the fluorescence damage comprises a crystal defect.

18. The solid state detector of claim 17, wherein the salt crystal comprises lithium fluoride.

19. The solid state detector of claim 15, wherein the solid state detector is optically transparent.

20. The solid state detector of claim 15, wherein the fluorescence damage emits light at a second wavelength in response to exposure of the solid state detector to a light source at a first wavelength.

* * * * *